(12) United States Patent
Cheng

(10) Patent No.: US 6,923,778 B1
(45) Date of Patent: Aug. 2, 2005

(54) MEDICAL SLING

(76) Inventor: Pay-Zen Cheng, 6750 W. Gate, Beaumont, TX (US) 77706

( * ) Notice: Subject to any disclaimer, the term of this patent is extended or adjusted under 35 U.S.C. 154(b) by 26 days.

(21) Appl. No.: 10/805,395

(22) Filed: Mar. 22, 2004

(51) Int. Cl.[7] .................................................. A61F 5/00
(52) U.S. Cl. .............................. 602/4; 602/20; 128/845
(58) Field of Search .............................. 602/4, 6, 5, 20, 602/60–63; 2/44, 45; 128/877, 878, 879, 128/845, 881, 882; D29/120.1, 121, 100, D29/122; D2/90.1; D24/190

(56) References Cited

U.S. PATENT DOCUMENTS 5,728,057 A * 3/1998 Ouellette et al. ............. 602/62
6,447,470 B2 * 9/2002 Bodenschatz et al. ........ 602/75
6,485,445 B1 * 11/2002 Hiltner ............................ 602/4
6,595,936 B1 * 7/2003 Oladipo ........................... 602/4

* cited by examiner

*Primary Examiner*—Kim M. Lewis
(74) *Attorney, Agent, or Firm*—Machetta Law Firm, P.C.; Gary M. Machetta

(57) ABSTRACT

The present invention relates to a sling device which is provided in a long tubular supply and is cut to the specific length needed for a user. This invention eliminates the need to stock various size slings for different size users. The material can be made of various types of elastic material and contains a reinforcement section. The user would insert their hand into the first slit and then remove the hand from another slit in the material so that the arm or forearm is covered. The sling would then be supported by being tied behind the neck.

4 Claims, 2 Drawing Sheets

MEDICAL SLING

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON A COMPACT DISC

Not Applicable

FIELD OF THE INVENTION

The present invention relates to a sling device for supporting an arm of a user. More particularly, the present invention relates to a sling device secured behind the neck of the user and designed so that the material can be cut to fit any size user.

DESCRIPTION OF RELATED ART

A sprained or broken arm requires support of the patients arm in a position which will prevent strain on the shoulder joint of the patient's injured arm. Typically, sling devices have consisted of a cloth sheet for around the user's neck. Sling devices have been provided in multiple sizes to fit various size users. This requires hospitals, medical facilities, doctor's offices, etc. to stock all the various sizes. In addition, sling devices are made of materials that begin to break apart if they are cut.

The present invention overcomes the aforementioned problem of stocking various sizes associated with the prior art sling devices by providing a sling device that can be designed for each specific user. This will eliminate the requirement to stock various size slings. Therefore it is a primary objective of the present invention to provide a single, flexible sling device that can fit various size users. A one-size fits all concept.

In addition, the present invention provides a reinforcement material to allow for cutting of the sling for various size arms or forearms and preventing breaking apart of the material of sling. Other advantages of the present invention will be readily apparent to those skilled in the art by a consideration of the detailed description contained hereinafter taken in conjunction with the annexed drawings.

BRIEF SUMMARY OF THE INVENTION

The present invention relates to a sling device which is provided in a long tubular supply and is cut to the specific length needed for a user. The material is made of an elastic material and contains a reinforcement section. The reinforcement section contains multiple layers of material. The reinforcement section is designed to prevent tearing or breaking apart of the sling when a cut is made within the sling to enlarge a slit for insertion of a hand. The user would insert their hand into the slit and then remove the hand from another slit in the material so that the arm or forearm is covered. The slits shall be spaced at an interval at or around two inches to provide adequate adjustment as necessary by selecting a slit that provides a firm fit. Next, the tube shaped material shall be attached behind the neck and tied to support the sling. This sling device does not include straps. Additional tube shaped material from the long tubular supply shall be provided as necessary to immobilize the arm or forearm. Lastly, the long tubular supply can be further used for additional medical slings.

The tube material shall be provided in a supply of length 10 feet to 300 feet. The long tubular supply will thus provide several Medical Slings of various sizes. The 10 feet length would likely provide 2 to 4 individual medical slings and the 300 feet length of supply would provide several dozen individual medical slings. This long tubular material will prevent hospitals, medical facilities, doctor's offices, etc. from having to stock all the various sizes for differing size individuals. The tube shaped material should have elastic properties allowing it to stretch from a 2 inch diameter to a 7 inch diameter as this is the typical size range for various individuals. In addition, to preventing the material from breaking apart, the tube shaped material shall contain between 5% cotton and 40% cotton. In the alternative, the tube shaped material may contain over 50% polyester and between 2% and 15% nylon to provide similar type properties and prevent tearing. The tube shaped material may also be provided with at least 30% cotton to ensure the strength needed.

BRIEF DESCRIPTION OF THE SEVERAL VIEWS OF THE DRAWING(S)

DETAILED DESCRIPTION OF THE INVENTION

Figure 1:
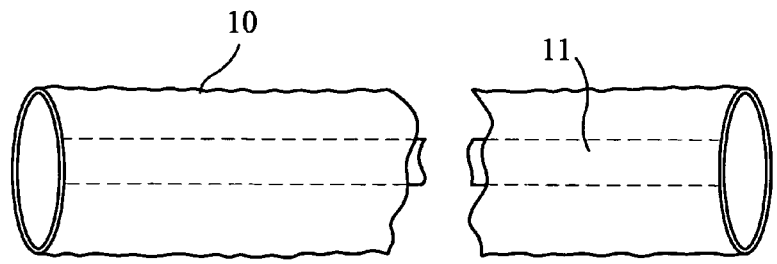
FIG. 1 is a front elevational view of a sling device according to the present invention.

FIG. 1 shows a front elevational view of a sling device 10 according to the present invention. The sling device 10 includes a reinforcement section 11. The sling device 10 is made of a non-woven elastic material that is breathable.

Figure 2:
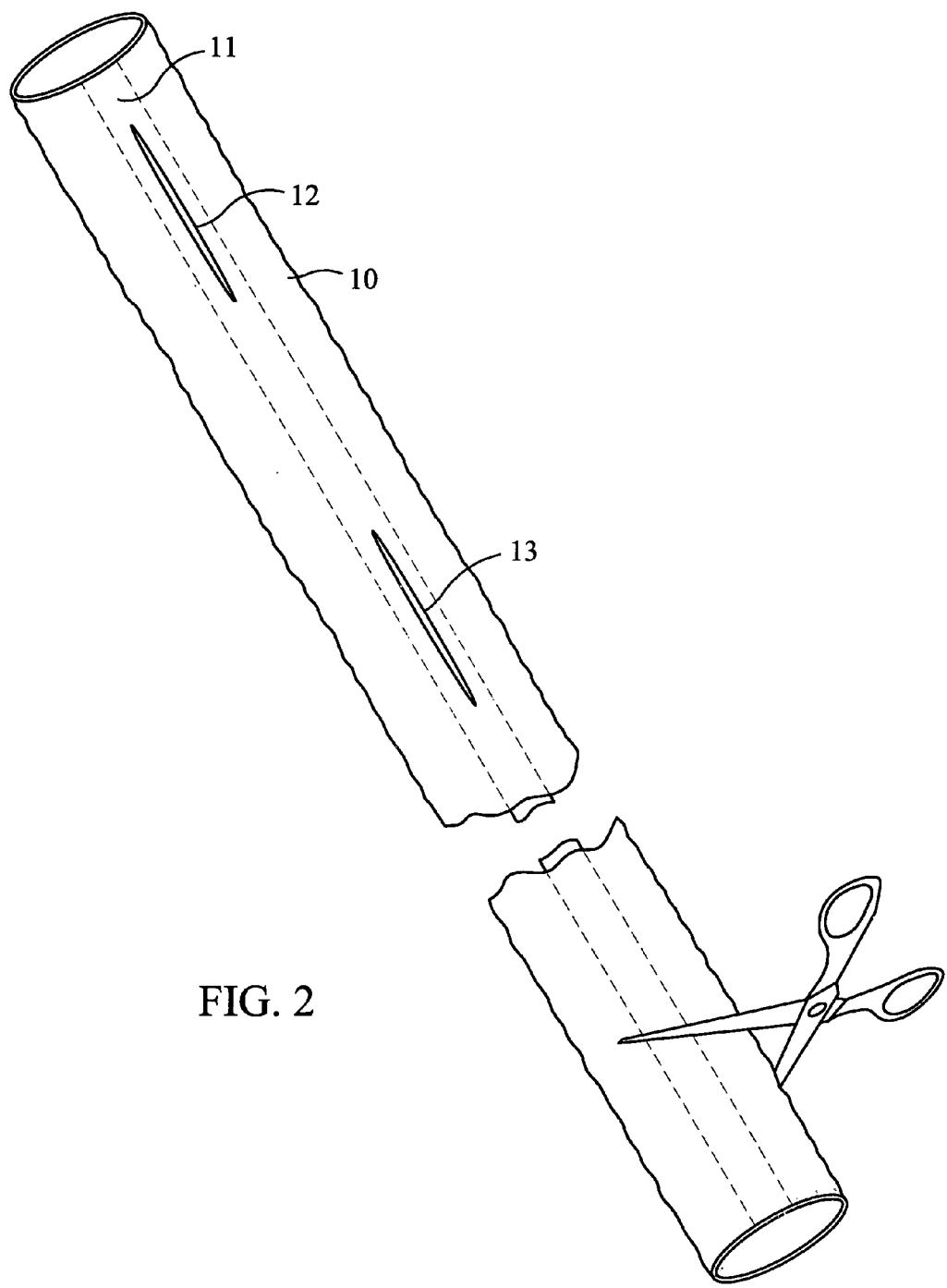
FIG. 2 is a side view of the sling device shown in FIG. 1.

FIG. 2 is a side view of the sling device 10 shown in FIG. 1. The slits 12 and 13 are shown within the reinforcement section 11 that travels the length of the sling device 10. Slits are provided at regular distances to adjust for varying size arms or forearms. The slit 12 is where the users hand would be inserted and then would exit slit 13 or another slit depending on the size of the arm or forearm. The slits 12 and 13 could be increased in size as needed. The sling device is cut to the appropriate length, depending on the user's needs, as shown. The reinforcement section 11 would prevent the sling device 10 from weakening and tearing apart from the enlarged slits.

Figure 3:
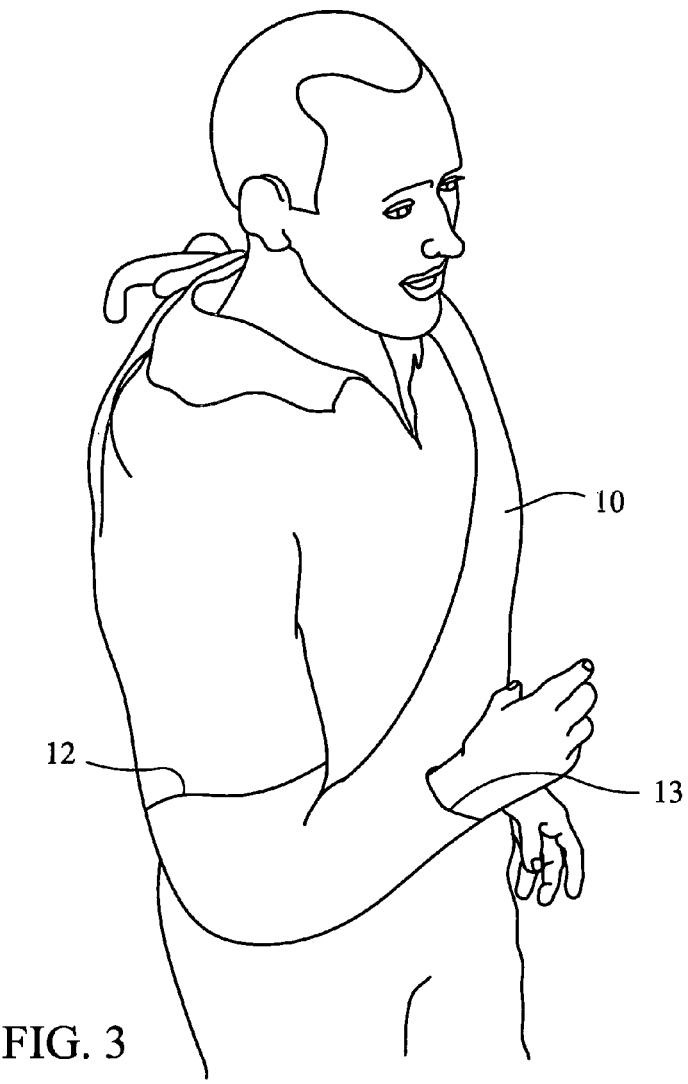
FIG. 3 is a perspective view of the sling as in FIG. 1 with a person's arm being supported and tied around the neck.

FIG. 3 is a perspective view of the sling device 10 as in FIG. 1 with a person's arm being supported and tied around the neck. The hand is shown extending through the slits 12 and 13.

What is claimed is:
1. A sling device comprising:
   (i) a tube shaped material manufactured from a non-woven substance with elastic like properties;
   (ii) said tube shaped material allowing for breathing;
   (iii) a reinforcement section along the entire length of said tube shaped material;

(iv) a plurality of slits centered within said reinforcement section and equally spaced; and (vi) wherein said tube shaped material has elastic properties allowing it to stretch from a 2 inch diameter to a 7 inch diameter.

2. A sling device according to claim 1, (i) wherein said tube shaped material is provided in a supply of length 10 ft to 300 ft.

3. A sling device comprising:

(i) a tube shaped material manufactured from a non-woven material wherein said tube shaped material is provided in a supply of length 10 ft to 300 ft (ii) said tube shaped material stretching from 2 inches to 7 inches;

(iii) a reinforcement section along the entire length of said tube shaped material including additional material;

(iv) a plurality of slits centered within said reinforcement section; and (v) said plurality of slits equally spaced at or around 2 inch intervals.

4. A process of supporting a sprained or broken arm by:

(i) cutting a specific length of tube shaped material to fit a user;

(ii) cutting two slits to allow for inserting the users hand into a first slit and out of second slit to cover an arm or forearm;

(iii) attaching the tube shaped material behind the neck by tieing the tube shaped material to support the sling;

(iv) applying additional tube shaped material as necessary to immobilize the arm or forearm; and (v) repeating the steps above as necessary to form multiple slings from the supply of tube shaped material.

* * * * *